United States Patent
Dunne (10) Patent No.: US 9,259,540 B2
(45) Date of Patent: Feb. 16, 2016

(54) NOZZLE AND INHALER AND METHOD FOR PRODUCING A NOZZLE

(71) Applicant: Stephen Terence Dunne, Stowmarket (GB)

(72) Inventor: Stephen Terence Dunne, Stowmarket (GB)

(73) Assignee: Boehringer Ingelheim Pharma GmbH & Co. KG, Ingelheim am Rhein (DE)

( * ) Notice: Subject to any disclaimer, the term of this patent is extended or adjusted under 35 U.S.C. 154(b) by 0 days.

(21) Appl. No.: 14/078,753

(22) Filed: Nov. 13, 2013

(65) Prior Publication Data

US 2014/0076308 A1 Mar. 20, 2014

Related U.S. Application Data

(63) Continuation of application No. 13/770,035, filed on Feb. 19, 2013, which is a continuation of application No. 12/812,685, filed as application No. PCT/EP2009/000252 on Jan. 16, 2009.

(30) Foreign Application Priority Data

Jan. 16, 2008 (GB) .................................. 0800709.8

(51) Int. Cl.
*A61M 11/00* (2006.01)
*A61M 15/00* (2006.01)
(Continued)

(52) U.S. Cl.
CPC .............. *A61M 11/00* (2013.01); *A61M 11/002* (2014.02); *A61M 11/007* (2014.02); *A61M 11/02* (2013.01); *A61M 11/04* (2013.01); *A61M 15/009* (2013.01); *A61M 15/0021* (2014.02); *A61M 15/0045* (2013.01); *A61M 15/0065* (2013.01);
(Continued)

(58) Field of Classification Search
CPC ... A61M 11/00; A61M 15/009; A61M 11/02; A61M 11/06; A61M 15/08; A61M 11/005; A61M 11/007; A61M 15/002; A61M 11/04; A61M 2202/064; A61M 2210/0618; A61M 15/0021; A61M 11/001; A61M 11/006; A61M 11/08; A61M 15/0086; A61M 15/0075; A61M 16/18; A61M 16/0063; A61M 15/00–15/0085
USPC ........ 128/200.15–200.23; 239/544–545, 596, 239/601
See application file for complete search history.

(56) References Cited

U.S. PATENT DOCUMENTS 2,785,926 A 3/1957 Lataste
5,358,179 A 10/1994 Lund et al.
(Continued)

FOREIGN PATENT DOCUMENTS

GB 2225809 A 6/1990
JP 10246946 A 9/1998
(Continued)

OTHER PUBLICATIONS

English language abstract of JP10246946.
(Continued)

*Primary Examiner* — Loan H Thanh
*Assistant Examiner* — Andrew S Lo
(74) *Attorney, Agent, or Firm* — Michael P. Morris; Mary-Ellen M. Devlin (57) ABSTRACT

A nozzle, an inhaler with a nozzle and a method for producing a nozzle are proposed, which nozzle comprises two holes formed in a flat plate which plate is then deformed such that the axes of the holes intersect so that jets of fluids moving through the holes impinge with each other.

6 Claims, 4 Drawing Sheets

(51) Int. Cl.
*B05B 1/26* (2006.01)
*A61M 11/02* (2006.01)
*A61M 11/04* (2006.01)
*B05B 11/00* (2006.01)

(52) U.S. Cl.
CPC .............. *B05B 1/26* (2013.01); *B05B 11/3091* (2013.01); *A61M 2202/0468* (2013.01); *B05B 11/3001* (2013.01)

(56) References Cited

U.S. PATENT DOCUMENTS

| | | | |
|---|---|---|---|
| 5,890,661 | A | 4/1999 | Crampton et al. |
| 6,322,008 | B1 | 11/2001 | Aker et al. |
| 6,584,335 | B1 | 6/2003 | Haar |
| 2003/0075623 | A1 | 4/2003 | Bartels et al. |
| 2003/0075624 | A1 | 4/2003 | Reisinger |
| 2003/0209238 | A1 | 11/2003 | Peters et al. |
| 2004/0026528 | A1 | 2/2004 | Jenkins |
| 2004/0164186 | A1 | 8/2004 | Kladders et al. |
| 2004/0256487 | A1* | 12/2004 | Collins et al. ................. 239/338 |
| 2005/0224076 | A1* | 10/2005 | Pfichner et al. .......... 128/200.14 |
| 2006/0207591 | A1* | 9/2006 | Gallem et al. ........... 128/200.14 |
| 2007/0131801 | A1 | 6/2007 | Hedger |
| 2014/0076308 | A1 | 3/2014 | Dunne |

FOREIGN PATENT DOCUMENTS

| | | |
|---|---|---|
| JP | 11076871 A | 3/1999 |
| JP | 2001-513350 A | 9/2001 |
| JP | 2006073777 A | 3/2006 |
| WO | 9114468 A1 | 10/1991 |
| WO | 9400686 A1 | 1/1994 |
| WO | 99-07277 A1 | 2/1999 |
| WO | 2009095160 A1 | 8/2009 |

OTHER PUBLICATIONS

English language abstract of JP11076871.
International Search Report, Form PCT/ISA/210, for corresponding PCT/EP2009/000252.

* cited by examiner

NOZZLE AND INHALER AND METHOD FOR PRODUCING A NOZZLE

The present invention relates to a nozzle according to the preamble of claim 1, to an inhaler according to the preamble of claim 11 and to a method for producing a nozzle.

The present invention relates in particular to the dispensing of an inhalation formulation by means of a nozzle or an inhaler, preferably a gas free-metered dose inhaler.

US 2003/0075623 A1 describes a nozzle with one or more nozzle outlets for the atomisation of fluids. The nozzle consists of at least two plates which are connected together, possibly by a intermediate layer. At least a base plate has a grooved structure which connects an inlet to nozzle outlet(s). In one embodiment, two or more nozzle outlets are provided which are orientated in such a way that jets issuing from them impinge on one another. The nozzle is typically made from a silicon plate and a glass plate welded together to form the channels. A filter can be inbuilt.

The present invention relates in particular to active inhalers such as an inhaler sold under the brand name "Respimat" shown in its basic structure in WO 91/14468 A1 and in a specific embodiment in WO 97/12687 A1 (FIGS. 6a, 6b). The inhaler has a reservoir for a fluid, which is to be atomised, and a pressure generator with a drive spring for delivering and atomising the fluid. The known inhaler comprises a nozzle with at least two holes for generating at least two impinging jets of the inhalation formulation to be dispensed.

When an inhalation formulation is dispensed, usually only small amounts are discharged. The inhalation formulation has to be atomised in a very defined manner into very fine particles or droplets. Therefore, the nozzle for generating fine jets of the inhalation formulation has to meet very close tolerances and comprises very fine openings or holes.

The known nozzles are difficult to produce and/or result in high manufacturing costs.

Object of the present invention is to provide a nozzle for generating at least two impinging jets, and an inhaler with such a nozzle, and a method for producing a nozzle, wherein production is facilitated and/or low production costs are possible.

The above object is achieved by a nozzle according to claim 1, by an inhaler according to claim 11 or by a method according to claim 12. Preferred embodiments are subject of the subclaims.

Preferably, two or more holes are formed in a thin metal plate and, then, the plate is deformed such that the axes of the holes intersect each other at a distance from the plate surface and/or at the outlet side of the nozzle.

The holes may be formed by drilling, laser drilling, punching or in any other suitable way.

The plate is preferably deformed after the holes have been formed or drilled. Thus, the holes can be formed or drilled into a flat plate, in particular with axes parallel to each other or perpendicular to the plate. This facilitates production. However, it is also possible to form, drill or open the holes after the plate has been deformed or without deformation of the plate.

In particular, the plate has a thickness of less than 200 μm, preferably of about 10 to 100 μm.

Preferably, the holes have respectively a hydraulic diameter of 2 to 100 μm, in particular of 3 to 30 μm, more preferably between 5 and 15 μm.

The distance between the holes is in particular about between 10 and 300 μm, preferably about 50 and 200 μm.

Preferably, the nozzle is formed only by the plate, and/or made of only one single component or piece, e.g. the plate.

According to a further aspect of the present invention, which can be realized independently, the nozzle is provided in particular by laser drilling with at least one hole, preferably two holes inclined to each other, in the preferably flat plate. The at least one hole is provided preferably with a smooth inlet region or entry area and preferably with a taper towards its outlet side which helps to ensure that a jet of fluid formed by the hole is essentially unbroken, e.g. until the jet impacts with another jet.

Thus, a simple construction of the nozzle can be achieved and/or low production costs are possible. Further, relatively easy production is possible even if close tolerances have to be met.

Further aspects, features, properties and advantages of the present invention are described in the claims and the subsequent description of preferred embodiments with reference to the drawing. There are shown in:

In the Figures, the same reference numbers are used for identical or similar parts, even if a repeated description is omitted. In particular identical or corresponding advantages and properties then also result or may be achieved.

Figure 1:
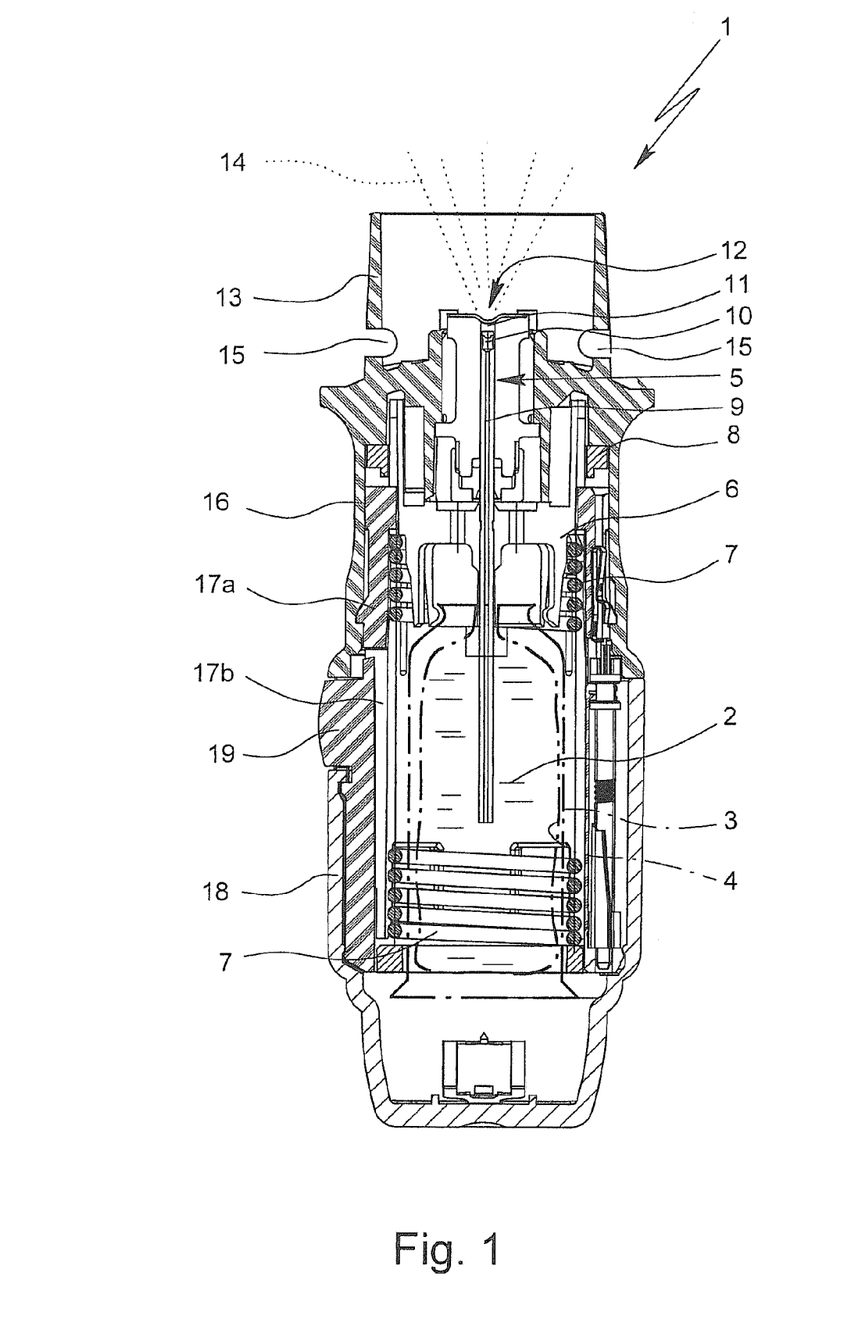
FIG. 1 a schematic section of an inhaler in the non-tensioned state.
Figure 2:
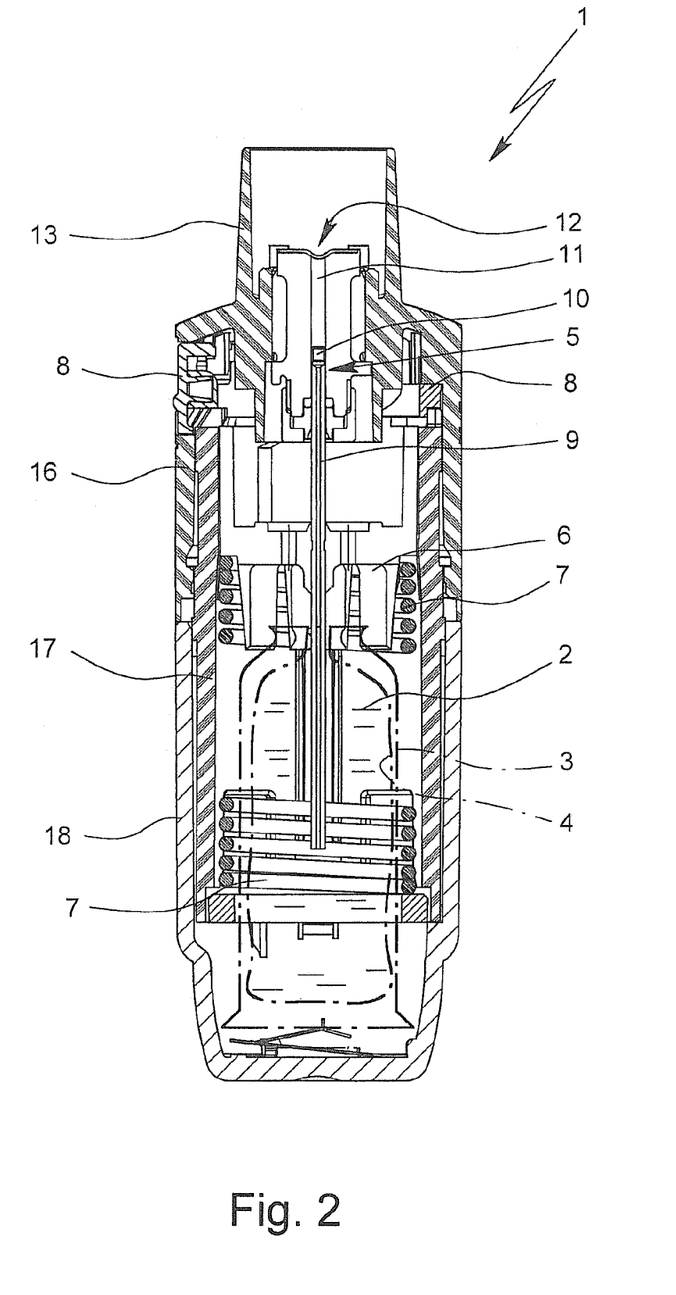
FIG. 2 a schematic section, rotated by 90° compared with FIG. 1, of the inhaler in the tensioned state.

FIGS. 1 and 2 show an inhaler 1 according to the present invention for atomising an inhalation formulation 2 as an aerosol 14, particularly a highly effective pharmaceutical composition or the like, diagrammatically shown in a non-tensioned state (FIG. 1) and in a tensioned state (FIG. 2).

The term "aerosol" in this respect is not limited to an inhalation formulation in liquid from, but also encompasses powder formulations.

The inhaler 1 is constructed in particular as a portable inhaler and preferably operates without propellant gas. Preferably, the inhaler 1 is portable, works only mechanically and/or is hand-held. However, the present invention may also be applied to inhalers 1 using a propellant, such as so-called MDIs (metered dose inhalers), a gas, such as compressed or liquefied gas or air, or the like, i.e. in particular to all kind of inhalers 1.

The inhalation formulation 2 is preferably a liquid, in particular a solution, suspension or suslution (mixture of solution and suspension), but can have any form and can be e.g. a powder or the like.

When the inhalation formulation 2, preferably a liquid, more particularly a pharmaceutical composition, is nebulised, an aerosol 14 is formed, which can be breathed in or inhaled by a user (not shown). Usually the inhaling is done at least once a day, more particularly several times a day, preferably at set intervals, depending on the complain from which the patient is suffering.

The inhaler 1 has in particular an insertable and preferably exchangeable container 3 containing the inhalation formulation 2. The container thus forms a reservoir for the inhalation formulation 2, which is to be nebulised. Preferably, the container 3 contains an amount of inhalation formulation 2 or active substance which is sufficient to provide up to 200 dosage units, for example, i.e. to allow up to 200 sprays or applications. A typical container 3, as disclosed in WO 96/06011 A1, holds a volume of about 2 to 10 ml.

The container 3 is substantially cylindrical or cartridge-shaped and once the inhaler 1 has been opened the container can be inserted therein from below and changed if desired. It is preferably of rigid construction, the inhalation formulation 2 in particular being held in a collapsible bag 4 in the container 3.

The inhaler 1 has a conveying means, such as a propellant, a pump, an air pump or any other pressure generator or compressed or liquefied gas, in particular a pump or pressure generator 5 for conveying gas, any other fluid and/or the inhalation formulation 2 and for nebulising the inhalation formulation 2, particularly in a preset and optionally adjustable dosage amount.

The inhalation formulation 2 may be metered in the inhaler 1 as it is the case in the present embodiment or may be pre-metered in an appropriate storage means, such as a blister with multiple blister pockets or the like.

In the present embodiment, the pressure generator 5 has preferably a holder 6 for the container 3, an associated drive spring 7, only partly shown, with a locking element 8 which can be manually operated to release it, a conveying member, preferably a conveying tube 9, a non-return valve 10 and/or a pressure chamber 11. The inhaler 1 comprises further nozzle 12 preferably in the region of a mouthpiece 13. The nozzle 12 will be described later in more detail. The container 3 is fixed in the inhaler 1 via the holder 6 such that the conveying tube 9 penetrates into the container 3. The holder 6 may be constructed so that the container 3 is able to be exchanged.

As the drive spring 7 is axially tensioned the holder 6 with the container 3 and the conveying tube 9 is moved downwards in the drawings, and the inhalation formulation 2 is sucked out of the container 3 into the pressure chamber 11 of the pressure generator 5 through the non-return valve 10. Preferably, the valve 10 is attached to or formed by the conveying tube 9.

After actuation of the locking element 8 the inhalation formulation 2 in the pressure chamber 11 is put under pressure as the conveying tube 9 with its now closed non-return valve 10 is moved back upwards by the relaxation of the drive spring 7 and now acts as a pressing ram or piston. This pressure forces the inhalation formulation 2 through the expulsion or dispensing nozzle 12, whereupon the formulation 2 is nebulised into an aerosol 14, as shown in FIG. 1.

Preferably the inhaler 1 may have a spring pressure of 5 to 200 MPa, preferably 10 to 100 MPa on the fluid, and/or a volume of fluid delivered per stroke of 5 to 100 µl, preferably 10 to 30 µl, most preferably about 15 µl. The fluid is converted into the aerosol 14 the droplets of which have an aerodynamic diameter of up to 20 µm, preferably 3 to 10 µm. The nozzle 12 has preferably a spray angle of 20° to 160°, preferably 80° to 100°.

A user (not shown) can inhale the aerosol 14, while an air supply is sucked into the mouthpiece 13 through preferably at least one air supply opening 15, preferably multiple air supply openings 15. Thus, a bypass is formed so that ambient air can be sucked into the mouthpiece 13.

The inhaler 1 comprises preferably an upper housing part 16 and an inner part 17 which is rotatable relative thereto (FIG. 2) having an upper part 17a and a lower part 17b (FIG. 1), while an in particular manually operable housing part 18 is releasably fixed, particularly fitted onto the inner part 17, preferably by means of a retaining element 19. In order to insert and/or replace the container 3 the housing part 18 can be detached from the inhaler 1.

Figure 3:
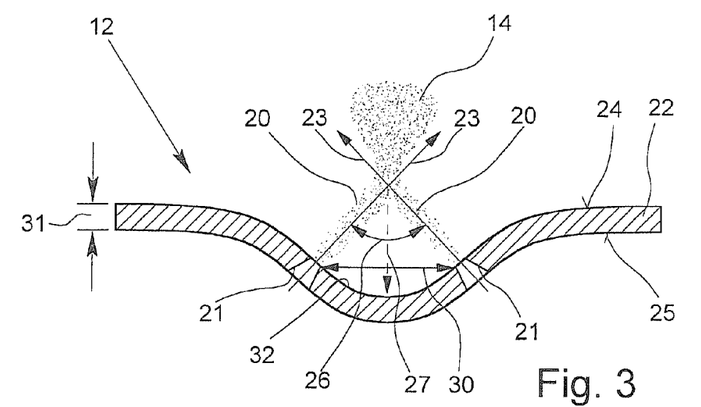
FIG. 3 a schematic section of a nozzle of the inhaler.

FIG. 3 shows in a very schematic sectional view (not in scale) the nozzle 12 in a preferred embodiment according to the present invention. This nozzle 12 is preferably mounted in or at the inhaler 1 previously described or any other inhaler 1. The mounting means are not shown. The nozzle 12 can be mounted e.g. by clamping or in any other suitable manner.

The nozzle 12 is for generating at least two impinging jets 20 of the fluid to be dispensed, here the inhalation formulation 2, as schematically shown in FIG. 3. The jets 20 intersect each other at the outlet side of the nozzle 12 or inhaler 1 and/or in a predetermined point or collision area, spaced from the plate 22.

The nozzle 12 comprises at least two holes 21 for dispensing the fluid, i.e. the inhalation formulation 2 in order to generate the jets 20 of the fluid.

The nozzle 12 comprises a plate 22 which may be formed by any plate portion of a component not shown or the like or which may be a separate or the sole component of the nozzle 12.

The holes 21 are formed in the plate 22. Preferably, the holes 21 are formed by drilling, in particular laser drilling, or punching of the plate 22.

Figure 4:
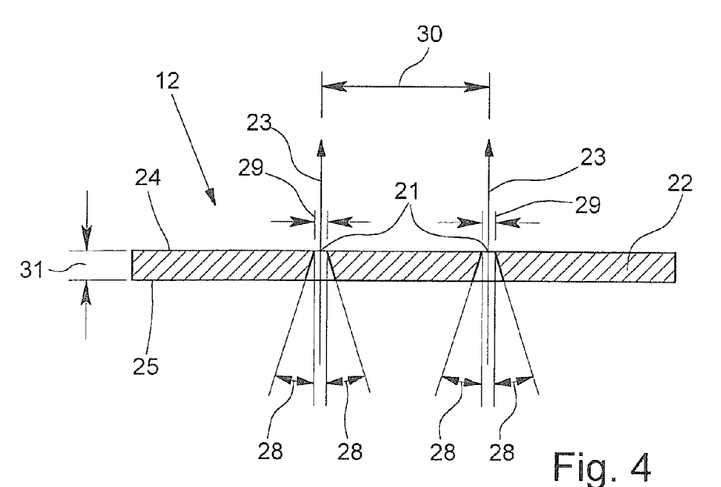
FIG. 4 a schematic section of a flat plate of the nozzle before deformation.
Figure 5:
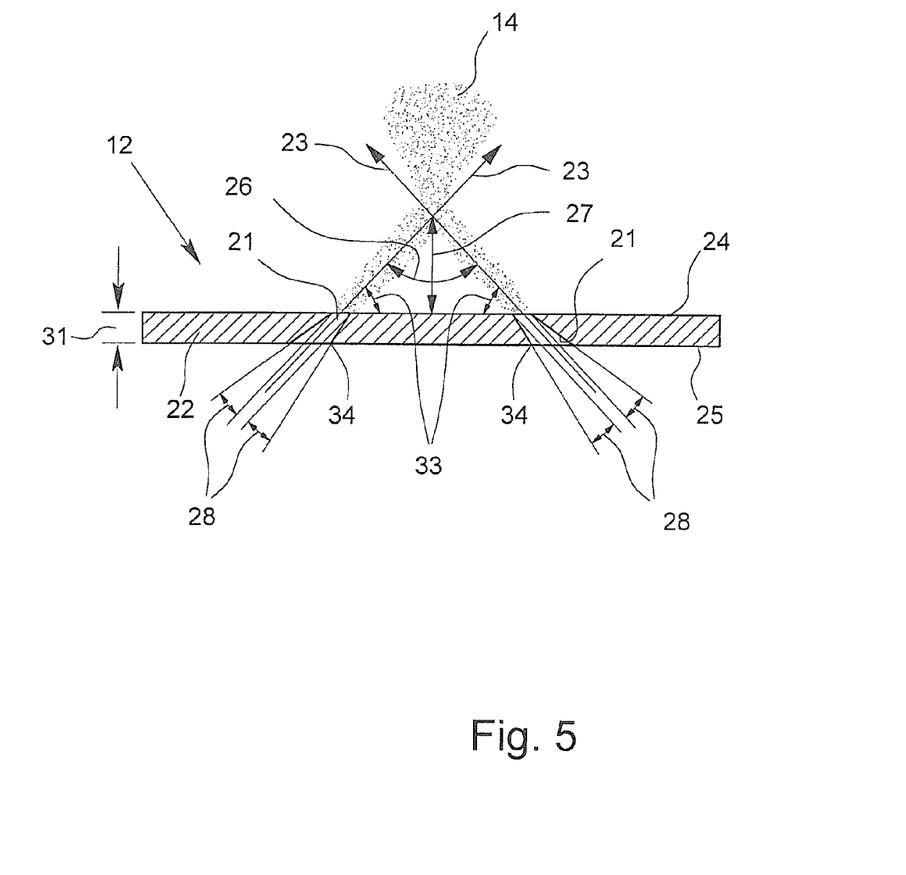
FIG. 5 a schematic section of another nozzle.

Preferably, the holes 21 are formed in the initially flat plate 22 as schematically shown in FIG. 4 which shows also a schematic sectional view of the nozzle 12 or plate 22.

It has to be pointed out that the production of the nozzle 12 is easy. The holes 21 can be formed easily by any suitable manner in the flat plate 22 before deformation.

The holes 21 are preferably formed such that their axes 23 (shown by arrows) run at least essentially parallel to each other and/or at least essentially perpendicular to the main plane of the plate 22 and/or do not intersect when the holes 21 are formed in the plate 22.

Afterwards, the plate 22 is deformed such that the axes 23 of the holes 21 cross or intersect each other with an angle 26 and/or at a distance 27 as schematically shown in FIG. 3. The deformation is preferably achieved by deep drawing or in any other suitable manner. For example, the plate 22 could also be bended or folded, e.g. that it has a V-form, so that the axes 23 intersect.

The distance 27 is preferably about 50 to 500 µm, in particular about 100 to 300 µm.

The angle 26 of intersection of the jets 20 or axes 23 is preferably about 90 to 180 degrees, in particular about 100 to 150 degrees.

The holes 21 are preferably circular in cross section.

The holes 21 are preferably tapered, in particular such that its outlet diameter is smaller at the outlet side 24 of the nozzle 12 or plate 22 than on the inlet side 25 of the nozzle 12 or plate 22. In particular, the holes 21 have a natural cone or taper angle 28 as schematically indicated in FIG. 4. Preferably, the angle is about 5 to 20 degrees.

The mean and/or hydraulic diameter 29 of the holes 21 is preferably about 2 to 50 µm, in particular about 3 to 30 µm, more preferably between 5 and 15 µm.

The term "hydraulic diameter" shall be understood as the diameter of a circular cross section corresponding in areal size to an actual, in particular non-cirucular cross section.

The holes 21 are spaced from each other by a distance 30. This refers either to the distance of the axes 23 before deformation of the plate 22 as schematically shown in FIG. 4 or to the distance of the inner edges or centers of the holes 21 at the outlet side 24 of the deformed plate 22 as schematically shown in FIG. 3. The distance 30 is preferably about between 10 and 300 µm, in particular about between 50 and 200 µm.

The plate 22 is preferably made of metal, in particular of stainless steel, or ceramic, silicon or plastic. However, any other suitable material could be used as well.

The plate 22 is preferably thin. In particular it has a thickness 31 of less than 200 µm, preferably of about 10 to 100 µm.

The deformed plate 22 forms preferably a bowl-like depression 32, in particular wherein the holes 21 are located on opposite sides of the depression 32, as schematically shown in FIG. 3.

The depression 32 is preferably about 50 to 250 μm deep and/or preferably has a diameter of about 150 to 500 μm.

The fluid (inhalation formulation 2) flows from the inner surface or inlet side 25 to the outer surface or outlet side 24 through the holes 21 in the direction of the taper. The helps to ensure that the jets 20 are unbroken before they impact with each other in the impaction region.

The impaction of the jets 20 supports atomisation of the fluid into very fine doplets or particles and/or slows down the main propagation speed of the aerosol 14. Alternatively or additionally, the intersection of the jets 20 can support mixing of different fluids if the jets 20 consist of different fluids.

FIG. 5 shows in a schematic sectional view similar to FIG. 3 another embodiment of the nozzle 12. Here, the plate 22 is flat, i.e. not deformed. The holes 21 are directly inclined, i.e. formed with an angle 33 relative to the main plane of plate 22 (e.g. half of intersection angle 26), so that the axes 23 of the holes 21 intersect each other at the outlet side 24 of the nozzle 12 as already described above.

The holes 21 are preferably laser drilled.

The holes 21 comprise preferably the same taper as previously described. This helps to ensure that the jets 20 are unbroken before impact.

The holes 21 preferably comprise a smooth entry or inlet region 34 (e.g. a rounded or tapered or inclined edge) which helps to ensure that the jets 20 are unbroken before impact at the distance 27 from plate 22 where atomization takes place.

The thickness 31 of the plate 22 is preferably between 10 and 150 μm.

The hydraulic diameter 29 of the holes 21 is preferably between 5 and 30 μm.

It has to be noted that the aspects and features of the different embodiments and alternatives and the different embodiments itself can be combined in any desired manner and/or independently from each other.

Some preferred ingredients and/or compositions of the preferably medicinal formulation 2 are listed below. As already mentioned, they are in particular powders or liquids in the broadest sense. Particularly preferably the formulation 2 contains the following:

The compounds listed below may be used in the device according to the invention on their own or in combination. In the compounds mentioned below, W is a pharmacologically active substance and is selected (for example) from among the betamimetics, anticholinergics, corticosteroids, PDE4-inhibitors, LTD4-antagonists, EGFR-inhibitors, dopamine agonists, H1-antihistamines, PAFantagonists and P13-kinase inhibitors. Moreover, double or triple combinations of W may be combined and used in the device according to the invention.

Combinations of W might be, for example:

- W denotes a betamimetic, combined with an anticholinergic, corticosteroid, PDE4-inhibitor, EGFR-inhibitor or LTD4-antagonist,
- W denotes an anticholinergic, combined with a betamimetic, corticosteroid, PDE4-inhibitor, EGFR-inhibitor or LTD4-antagonist,
- W denotes a corticosteroid, combined with a PDE4-inhibitor, EGFR-inhibitor or LTD4-antagonist
- W denotes a PDE4-inhibitor, combined with an EGFR-inhibitor or LTD4-antagonist
- W denotes an EGFR-inhibitor, combined with an LTD4-antagonist.

The compounds used as betamimetics are preferably compounds selected from among albuterol, arformoterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmefamol, salmeterol, soterenol, sulphonterol, terbutaline, tiaramide, tolubuterol, zinterol, CHF-1035, HOKU-81, KUL-1248 and 3-(4-{6-[2-hydroxy-2-(4-hydroxy-3-hydroxymethyl-phenyl)-ethylamino]-hexyloxy}-butyl)-benzyl-sulphonamide 5-[2-(5.6-diethyl-indan-2-ylamino)-1-hydroxy-ethyl]-8-hydroxy-1H-quinolin-2-one 4-hydroxy-7-[2-{[2-{[3-(2-phenylethoxy)propyl] sulphonyl}ethyl]-amino}ethyl]-2(3H)-benzothiazolone 1-(2-fluoro-4-hydroxyphenyl)-2-[4-(1-benzimidazolyl)-2-methyl-2-butylamino]ethanol 1-[3-(4-methoxybenzyl-amino)-4-hydroxyphenyl]-2-[4-(1-benzimidazolyl)-2-methyl-2-butylamino]ethanol 1-[2H-5-hydroxy-3-oxo-4H-1,4-benzoxazin-8-yl]-2-[3-(4-N,N-dimethylaminophenyl)-2-methyl-2-propylamino] ethanol 1-[2H-5-hydroxy-3-oxo-4H-1,4-benzoxazin-8-yl]-2-[3-(4-methoxyphenyl)-2-methyl-2-propylamino]ethanol 1-[2H-5-hydroxy-3-oxo-4H-1,4-benzoxazin-8-yl]-2-[3-(4-n-butyloxyphenyl)-2-methyl-2-propylamino]ethanol 1-[2H-5-hydroxy-3-oxo-4H-1,4-benzoxazin-8-yl]-2-{4-[3-(4-methoxy-phenyl)-1,2,4-triazol-3-yl]-2-methyl-2-butylamino}ethanol 5-hydroxy-8-(1-hydroxy-2-isopropylaminobutyl)-2H-1,4-benzoxazin-3-(4H)one 1-(4-amino-3-chloro-5-trifluoromethylphenyl)-2-tert.-butylamino)ethanol 6-hydroxy-8-{1-hydroxy-2-[2-(4-methoxy-phenyl)-1,1-dimethyl-ethylamino]-ethyl}-4H-benzo[1,4]oxazin-3-one 6-hydroxy-8-{1-hydroxy-2-[2-(ethyl 4-phenoxy-acetate)-1,1-dimethyl-ethylamino]-ethyl}-4H-benzo[1,4]oxazin-3-one 6-hydroxy-8-{1-hydroxy-2-[2-(4-phenoxy-acetic acid)-1,1-dimethyl-ethylamino]-ethyl}-4H-benzo[1,4]oxazin-3-one 8-{2-[1,1-dimethyl-2-(2.4.6-trimethylphenyl)-ethylamino]-1-hydroxy-ethyl}-6-hydroxy-4H-benzo[1,4]oxazin-3-one 6-hydroxy-8-{1-hydroxy-2-[2-(4-hydroxy-phenyl)-1,1-dimethyl-ethylamino]-ethyl}-4H-benzo[1,4]oxazin-3-one 6-hydroxy-8-{1-hydroxy-2-[2-(4-isopropyl-phenyl)-1.1-dimethyl-ethylamino]-ethyl}-4H-benzo[1,4]oxazin-3-one 8-{2-[2-(4-ethyl-phenyl)-1,1-dimethyl-ethylamino]-1-hydroxy-ethyl}-6-hydroxy-4H-benzo[1,4]oxazin-3-one 8-{2-[2-(4-ethoxy-phenyl)-1,1-dimethyl-ethylamino]-1-hydroxy-ethyl}-6-hydroxy-4H-benzo[1,4]oxazin-3-one 4-(4-{2-[2-hydroxy-2-(6-hydroxy-3-oxo-3.4-dihydro-2H-benzo[1,4]oxazin-8-yl)-ethylamino]-2-methyl-propyl}-phenoxy)-butyric acid 8-{2-[2-(3.4-difluoro-phenyl)-1,1-dimethyl-ethylamino]-1-hydroxy-ethyl}-6-hydroxy-4H-benzo[1,4]oxazin-3-one 1-(4-ethoxy-carbonylamino-3-cyano-5-fluorophenyl)-2-(tertbutylamino)ethanol 2-hydroxy-5-(1-hydroxy-2-{2-[4-(2-hydroxy-2-phenyl-ethylamino)-phenyl]-ethylamino}-ethyl)-benzaldehyde N-[2-hydroxy-5-(1-hydroxy-2-{2-[4-(2-hydroxy-2-phenyl-ethylamino)-phenyl]-ethylamino}-ethyl)-phenyl]-formamide 8-hydroxy-5-(1-hydroxy-2-{2-[4-(6-methoxy-biphenyl-3-ylamino)-phenyl]-ethylamino}-ethyl)-1H-quinolin-2-one 8-hydroxy-5-[1-hydroxy-2-(6-phenethylamino-hexylamino)-ethyl]-1H-quinolin-2-one 5-[2-(2-{4-[4-(2-amino-2-methyl-propoxy)-phenylamino]-phenyl}-ethylamino)-1-hydroxy-ethyl]-8-hydroxy-1H-quinolin-2-one
[3-(4-{6-[2-hydroxy-2-(4-hydroxy-3-hydroxymethyl-phenyl)-ethylamino]-hexyloxy}-butyl)-5-methyl-phenyl]-urea
4-(2-{6-[2-(2.6-dichloro-benzyloxy)-ethoxy]-hexylamino}-1-hydroxy-ethyl)-2-hydroxymethyl-phenol
3-(4-{6-[2-hydroxy-2-(4-hydroxy-3-hydroxymethyl-phenyl)-ethylamino]-hexyloxy}-butyl)-benzylsulphonamide
3-(3-{7-[2-hydroxy-2-(4-hydroxy-3-hydroxymethyl-phenyl)-ethylamino]-heptyloxy}-propyl)-benzylsulphonamide
4-(2-{6-[4-(3-cyclopentanesulphonyl-phenyl)-butoxy]-hexylamino}-1-hydroxyethyl)-2-hydroxymethyl-phenol
N-Adamantan-2-yl-2-(3-{2-[2-hydroxy-2-(4-hydroxy-3-hydroxymethylphenyl)-ethylamino]-propyl}-phenyl)-acetamide optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-ptoluenesulphonate.

The anticholinergics used are preferably compounds selected from among the tiotropium salts, preferably the bromide salt, oxitropium salts, preferably the bromide salt, flutropium salts, preferably the bromide salt, ipratropium salts, preferably the bromide salt, glycopyrronium salts, preferably the bromide salt, trospium salts, preferably the chloride salt, tolterodine. In the above-mentioned salts the cations are the pharmacologically active constituents. As anions the above-mentioned salts may preferably contain the chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts the chlorides, bromides, iodides and methanesulphonates are particularly preferred.

Other preferred anticholinergics are selected from among the salts of formula AC-1

AC-1 wherein X⁻ denotes an anion with a single negative charge, preferably an anion selected from among the fluoride, chloride, bromide, iodide, sulphate, phosphate, methanesulphonate, nitrate, maleate, acetate, citrate, fumarate, tartrate, oxalate, succinate, benzoate and p-toluenesulphonate, preferably an anion with a single negative charge, particularly preferably an anion selected from among the fluoride, chloride, bromide, methanesulphonate and p-toluenesulphonate, particularly preferably bromide, optionally in the form of the racemates, enantiomers or hydrates thereof. Of particular importance are those pharmaceutical combinations which contain the enantiomers of formula AC-1-en

AC-1-en wherein X⁻ may have the above-mentioned meanings. Other preferred anticholinergics are selected from the salts of formula AC-2

AC-2 wherein R denotes either methyl or ethyl and wherein X⁻ may have the above-mentioned meanings. In an alternative embodiment the compound of formula AC-2 may also be present in the form of the free base AC-2-base.

AC-2-base

Other specified compounds are:
tropenol 2,2-diphenylpropionate methobromide,
scopine 2,2-diphenylpropionate methobromide,
scopine 2-fluoro-2,2-diphenylacetate methobromide,
tropenol 2-fluoro-2,2-diphenylacetate methobromide;
tropenol 3,3',4,4'-tetrafluorobenzilate methobromide,
scopine 3,3',4,4'-tetrafluorobenzilate methobromide,
tropenol 4,4'-difluorobenzilate methobromide,
scopine 4,4'-difluorobenzilate methobromide,
tropenol 3,3'-difluorobenzilate methobromide,
scopine 3,3'-difluorobenzilate methobromide;

tropenol 9-hydroxy-fluorene-9-carboxylate methobromide;
tropenol 9-fluoro-fluorene-9-carboxylate methobromide;
scopine 9-hydroxy-fluorene-9-carboxylate methobromide;
scopine 9-fluoro-fluorene-9-carboxylate methobromide;
tropenol 9-methyl-fluorene-9-carboxylate methobromide;
scopine 9-methyl-fluorene-9-carboxylate methobromide;
cyclopropyltropine benzilate methobromide;
cyclopropyltropine 2,2-diphenylpropionate methobromide;
cyclopropyltropine 9-hydroxy-xanthene-9-carboxylate methobromide;
cyclopropyltropine 9-methyl-fluorene-9-carboxylate methobromide;
cyclopropyltropine 9-methyl-xanthene-9-carboxylate methobromide;
cyclopropyltropine 9-hydroxy-fluorene-9-carboxylate methobromide;
cyclopropyltropine methyl 4,4'-difluorobenzilate methobromide.
tropenol 9-hydroxy-xanthene-9-carboxylate methobromide;
scopine 9-hydroxy-xanthene-9-carboxylate methobromide;
tropenol 9-methyl-xanthene-9-carboxylate-methobromide;
scopine 9-methyl-xanthene-9-carboxylate-methobromide;
tropenol 9-ethyl-xanthene-9-carboxylate methobromide;
tropenol 9-difluoromethyl-xanthene-9-carboxylate methobromide;
scopine 9-hydroxymethyl-xanthene-9-carboxylate methobromide, The above-mentioned compounds may also be used as salts within the scope of the present invention, wherein instead of the methobromide the salts methoX are used, wherein X may have the meanings given hereinbefore for X.

As corticosteroids it is preferable to use compounds selected from among beclomethasone, betamethasone, budesonide, butixocort, ciclesonide, deflazacort, dexamethasone, etiprednol, flunisolide, fluticasone, loteprednol, mometasone, prednisolone, prednisone, rofleponide, triamcinolone, RPR-106541, NS-126, ST-26 and (S)-fluoromethyl 6,9-difluoro-17-[(2-furanylcarbonyl)oxy]-11-hydroxy-16-methyl-3-oxo-androsta-1,4-diene-17-carbothionate (S)-(2-oxo-tetrahydro-furan-3S-yl)6,9-difluoro-11-hydroxy-16-methyl-3-oxo-17-propionyloxy-androsta-1,4-diene-17-carbothionate, cyanomethyl 6α,9α-difluoro-11β-hydroxy-16α-methyl-3-oxo-17α-(2,2,3,3-tetramethylcyclopropylcarbonyl)oxy-androsta-1,4-diene-17β-carboxylate optionally in the form of the racemates, enantiomers or diastereomers thereof and optionally in the form of the salts and derivatives thereof, the solvates and/or hydrates thereof. Any reference to steroids includes a reference to any salts or derivatives, hydrates or solvates thereof which may exist. Examples of possible salts and derivatives of the steroids may be: alkali metal salts, such as for example sodium or potassium salts, sulphobenzoates, phosphates, isonicotinates, acetates, dichloroacetates, propionates, dihydrogen phosphates, palmitates, pivalates or furoates.

PDE4-inhibitors which may be used are preferably compounds selected from among enprofyllin, theophyllin, roflumilast, ariflo (cilomilast), tofimilast, pumafentrin, lirimilast, arofyllin, atizoram, D-4418, Bay-198004, BY343, CP-325.366, D-4396 (Sch-351591), AWD-12-281 (GW-842470), NCS-613, CDP-840, D-4418, PD-168787, T-440, T-2585, V-11294A, CI-1018, CDC-801, CDC-3052, D-22888, YM-58997, Z-15370 and N-(3,5-dichloro-1-oxo-pyridin-4-yl)-4-difluoromethoxy-3-cyclopropylmethoxybenzamide (−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide (R)-(+)-1-(4-bromobenzyl)-4-[(3-cyclopentyloxy)-4-methoxyphenyl]-2-pyrrolidone 3-(cyclopentyloxy-4-methoxyphenyl)-1-(4-N'-[N-2-cyano-5-methylisothioureido]benzyl)-2-pyrrolidone cis[4-cyano-4-(3-cyclopentyloxy-4-methoxyphenyl)cyclohexane-1-carboxylic acid]

2-carbomethoxy-4-cyano-4-(3-cyclopropylmethoxy-4-difluoromethoxyphenyl)cyclohexan-1-one cis[4-cyano-4-(3-cyclopropylmethoxy-4-difluoromethoxyphenyl)cyclohexan-1-ol]

(R)-(+)-ethyl[4-(3-cyclopentyloxy-4-methoxyphenyl)pyrrolidin-2-ylidene]acetate (S)-(−)-ethyl[4-(3-cyclopentyloxy-4-methoxyphenyl)pyrrolidin-2-ylidene]acetate 9-cyclopentyl-5,6-dihydro-7-ethyl-3-(2-thienyl)-9H-pyrazolo[3,4-c]-1,2,4-triazolo[4.3-a]pyridine 9-cyclopentyl-5,6-dihydro-7-ethyl-3-(tert-butyl)-9H-pyrazolo[3,4-c]-1,2,4-triazolo[4.3-a]pyridine optionally in the form of the racemates, enantiomers or diastereomers thereof and optionally in the form of the pharmacologically acceptable acid addition salts thereof, the solvates and/or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The LTD4-antagonists used are preferably compounds selected from among montelukast, pranlukast, zafirlukast, MCC-847 (ZD-3523), MN-001, MEN-91507 (LM-1507), VUF-5078, VUF-K-8707, L-733321 and 1-(((R)-(3-(2-(6,7-difluoro-2-quinolinyl)ethenyl)phenyl)-3-(2-(2-hydroxy-2-propyl)phenyl)thio)methylcyclopropane-acetic acid, 1-(((1R)-3(3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropaneacetic acid

[2-[[2-(4-tert-butyl-2-thiazolyl)-5-benzofuranyl]oxymethyl]phenyl]acetic acid optionally in the form of the racemates, enantiomers or diastereomers thereof and optionally in the form of the pharmacologically acceptable acid addition salts, solvates and/or hydrates thereof. According to the invention the acid addition salts of the betamimetics are preferably selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-ptoluenesulphonate. By salts or derivatives which the LTD4-antagonists may optionally be capable of forming are meant, for example: alkali metal salts, such as for example sodium or potassium salts, alkaline earth metal salts, sulphobenzoates, phosphates, isonicotinates, acetates, propionates, dihydrogen phosphates, palmitates, pivalates or furoates.

EGFR-inhibitors which may be used are preferably compounds selected from among cetuximab, trastuzumab, ABX-EGF, Mab ICR-62 and 4-[(3-chloro-4-fluorophenyl)amino]-6-{[4-(morpholin-4-yl)-1-oxo-2-buten-1-yl]amino}-7-cyclopropylmethoxy-quinazoline 4-[(3-chloro-4-fluorophenyl)amino]-6-{[4-(N,N-diethylamino)-1-oxo-2-buten-1-yl]amino}-7-cyclopropylmethoxy-quinazoline 4-[(3-chloro-4-fluorophenyl)amino]-6-{[4-(N,N-dimethylamino)-1-oxo-2-buten-1-yl]amino}-7-cyclopropylmethoxy-quinazoline 4-[(R)-(1-phenyl-ethyl)amino]-6-{[4-(morpholin-4-yl)-1-oxo-2-buten-1-yl]-amino}-7-cyclopentyloxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline 4-[(3-chloro-4-fluoro-phenyl)amino]-6-[2-((S)-6-methyl-2-oxo-morpholin-4-yl)-ethoxy]-7-methoxy-quinazoline 4-[(3-chloro-4-fluorophenyl)amino]-6-({4-[N-(2-methoxy-ethyl)-N-methylamino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-cyclopentyloxy-quinazoline 4-[(R)-(1-phenyl-ethypamino]-6-{[4-(N,N-to-(2-methoxy-ethyl)-amino)-1-oxo-2-buten-1-yl]amino}-7-cyclopropylmethoxy-quinazoline 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline 4-[(R)-(1-phenyl-ethyl)amino]-6-({4-[N-(tetrahydropyran-4-yl)-N-methylamino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline 4-[(3-chloro-4-fluorophenyl)amino]-6-({4-[N-(2-methoxy-ethyl)-N-methylamino]-1-oxo-2-buten-1-yl}amino)-7-cyclopentyloxy-quinazoline 4-[(3-chloro-4-fluorophenyl)amino]-6-{[4-(N-cyclopropyl-N-methyl-amino)-1-oxo-2-buten-1-yl]amino}-7-cyclopentyloxy-quinazoline 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline 4-[(3-ethynyl-phenyl)amino]-6.7-to-(2-methoxy-ethoxy)-quinazoline 4-[(3-chloro-4-fluorophenyl)amino]-7-[3-(morpholin-4-yl)-propyloxy]-6-[(vinylcarbonyl)amino]-quinazoline 4-[(R)-(1-phenyl-ethyl)amino]-6-(4-hydroxy-phenyl)-7H-pyrrolo[2,3-d]pyrimidine 3-cyano-4-[(3-chloro-4-fluorophenyl)amino]-6-{[4-(N,N-dimethylamino)-1-oxo-2-buten-1-yl]amino}-7-ethoxy-quinoline 4-{[3-chloro-4-(3-fluoro-benzyloxy)-phenyl]amino}-6-(5-{[(2-methanesulphonyl-ethyl)amino]methyl}-furan-2-yl)quinazoline 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline 4-[(3-chloro-4-fluorophenyl)amino]-6-({4-[N,N-to-(2-methoxy-ethyl)-amino]-1-oxo-2-buten-1-yl}amino)-7-[(tetrahydrofuran-2-yl)methoxy]-quinazoline 4-[(3-ethynyl-phenyl)amino]-6-{[4-(5.5-dimethyl-2-oxo-morpholin-4-yl)-1-oxo-2-buten-1-yl]amino}-quinazoline 4-[(3-chloro-4-fluoro-phenyl)amino]-6-[2-(2,2-dimethyl-6-oxo-morpholin-4-yl)ethoxy]-7-methoxy-quinazoline 4-[(3-chloro-4-fluoro-phenyl)amino]-6-[2-(2,2-dimethyl-6-oxo-morpholin-4-yl)ethoxy]-7-[(R)-(tetrahydrofuran-2-yl)methoxy]-quinazoline 4-[(3-chloro-4-fluoro-phenyl)amino]-7-[2-(2,2-dimethyl-6-oxo-morpholin-4-yl)ethoxy]-6-[(S)-(tetrahydrofuran-2-yl)methoxy]-quinazoline 4-[(3-chloro-4-fluoro-phenyl)amino]-6-{2-[4-(2-oxo-morpholin-4-yl)-pipendin-1-yl]-ethoxy}-7-methoxy-quinazoline 4-[(3-chloro-4-fluoro-phenyl)amino]-6-[1-(tert.-butyloxycarbonyl)-piperidin-4-yloxy]-7-methoxy-quinazoline 4-[(3-chloro-4-fluoro-phenyl)amino]-6-(trans-4-amino-cyclohexan-1-yloxy)-7-methoxy-quinazoline 4-[(3-chloro-4-fluoro-phenyl)amino]-6-(trans-4-methanesulphonylaminocyclohexan-1-yloxy)-7-methoxy-quinazoline 4-[(3-chloro-4-fluoro-phenyl)amino]-6-(tetrahydropyran-3-yloxy)-7-methoxy-quinazoline 4-[(3-chloro-4-fluoro-phenyl)amino]-6-(1-methyl-piperidin-4-yloxy)-7-methoxy-quinazoline 4-[(3-chloro-4-fluoro-phenyl)amino]-6-{1-[(morpholin-4-yl)carbonyl]-piperidin-4-yloxy}-7-methoxy-quinazoline 4-[(3-chloro-4-fluoro-phenyl)amino]-6-{1-[(methoxymethyl)carbonyl]-piperidin-4-yloxy}-7-methoxy-quinazoline 4-[(3-chloro-4-fluoro-phenyl)amino]-6-(piperidin-3-yloxy)-7-methoxy-quinazoline 4-[(3-chloro-4-fluoro-phenyl)amino]-6-[1-(2-acetylamino-ethyl)-piperidin-4-yloxy]-7-methoxy-quinazoline 4-[(3-chloro-4-fluoro-phenyl)amino]-6-(tetrahydropyran-4-yloxy)-7-ethoxy-quinazoline 4-[(3-chloro-4-fluoro-phenyl)amino]-6-((S)-tetrahydrofuran-3-yloxy)-7-hydroxy-quinazoline 4-[(3-chloro-4-fluoro-phenyl)amino]-6-(tetrahydropyran-4-yloxy)-7-(2-methoxy-ethoxy)-quinazoline 4-[(3-chloro-4-fluoro-phenyl)amino]-6-{trans-4-[(dimethylamino)sulphonylamino]-cyclohexan-1-yloxy}-7-methoxyquinazoline 4-[(3-chloro-4-fluoro-phenyl)amino]-6-{trans-4-[(morpholin-4-yl)carbonylamino]-cyclohexan-1-yloxy}-7-methoxy-quinazoline 4-[(3-chloro-4-fluoro-phenyl)amino]-6-{trans-4-[(morpholin-4-yl)sulphonylamino]-cyclohexan-1-yloxy}-7-methoxy-quinazoline 4-[(3-chloro-4-fluoro-phenyl)amino]-6-(tetrahydropyran-4-yloxy)-7-(2-acetylamino-ethoxy)-quinazoline 4-[(3-chloro-4-fluoro-phenyl)amino]-6-(tetrahydropyran-4-yloxy)-7-(2-methanesulphonylamino-ethoxy)-quinazoline 4-[(3-chloro-4-fluoro-phenyl)amino]-6-{1-[(piperidin-1-yl)carbonyl]-piperidin-4-yloxy}-7-methoxy-quinazoline 4-[(3-chloro-4-fluoro-phenyl)amino]-6-(1-aminocarbonylmethyl-piperidin-4-yloxy)-7-methoxy-quinazoline 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)carbonyl]-Nmethyl-amino}-cyclohexan-1-yloxy)-7-methoxy-quinazoline 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline
4-[(3-chloro-4-fluoro-phenyl)amino]-6-(trans-4-ethanesulphonylaminocyclohexan-1-yloxy)-7-methoxy-quinazoline
4-[(3-chloro-4-fluoro-phenyl)amino]-6-(1-methanesulphonyl-piperidin-4-yloxy)-7-ethoxy-quinazoline
4-[(3-chloro-4-fluoro-phenyl)amino]-6-(1-methanesulphonyl-piperidin-4-yloxy)-7-(2-methoxy-ethoxy)-quinazoline
4-[(3-chloro-4-fluoro-phenyl)amino]-6-[1-(2-methoxyacetyl)-piperidin-4-yloxy]-7-(2-methoxy-ethoxy)-quinazoline
4-[(3-chloro-4-fluoro-phenyl)amino]-6-(cis-4-acetylaminocyclohexan-1-yloxy)-7-methoxy-quinazoline
4-[(3-ethynyl-phenyl)amino]-6-[1-(tert.-butyloxycarbonyl)-piperidin-4-yloxy]-7-methoxy-quinazoline
4-[(3-ethynyl-phenyl)amino]-6-(tetrahydropyran-4-yloxy]-7-methoxyquinazoline
4-[(3-chloro-4-fluoro-phenyl)amino]-6-(cis-4-{N-[(piperidin-1-yl)carbonyl]-Nmethyl-amino}-cyclohexan-1-yloxy)-7-methoxy-quinazoline
4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline
4-[(3-chloro-4-fluoro-phenyl)amino]-6-{cis-4-[(morpholin-4-yl)carbonylamino]-cyclohexan-1-yloxy}-7-methoxy-quinazoline
4-[(3-chloro-4-fluoro-phenyl)amino]-6-{1-[2-(2-oxopyrrolidin-1-yl)ethyl]-piperidin-4-yloxy}-7-methoxy-quinazoline
4-[(3-chloro-4-fluoro-phenyl)amino]-6-{1-[(morpholin-4-yl)carbonyl]-piperidin-4-yloxy}-7-(2-methoxy-ethoxy)-quinazoline
4-[(3-ethynyl-phenyl)amino]-6-(1-acetyl-piperidin-4-yloxy)-7-methoxyquinazoline
4-[(3-ethynyl-phenyl)amino]-6-(1-methyl-piperidin-4-yloxy)-7-methoxyquinazoline
4-[(3-ethynyl-phenyl)amino]-6-(1-methanesulphonyl-piperidin-4-yloxy)-7-methoxy-quinazoline
4-[(3-chloro-4-fluoro-phenyl)amino]-6-(1-methyl-piperidin-4-yloxy)-7(2-methoxy-ethoxy)-quinazoline
4-[(3-chloro-4-fluoro-phenyl)amino]-6-(1-isopropyloxycarbonyl-piperidin-4-yloxy)-7-methoxy-quinazoline
4-[(3-chloro-4-fluoro-phenyl)amino]-6-(cis-4-methylamino-cyclohexan-1-yloxy)-7-methoxy-quinazoline
4-[(3-chloro-4-fluoro-phenyl)amino]-6-{cis-4-[N-(2-methoxy-acetyl)-N-methylamino]-cyclohexan-1-yloxy}-7-methoxy-quinazoline
4-[(3-ethynyl-phenyl)amino]-6-(piperidin-4-yloxy)-7-methoxy-quinazoline
4-[(3-ethynyl-phenyl)amino]-6-[1-(2-methoxy-acetyl)-piperidin-4-yloxy]-7-methoxy-quinazoline
4-[(3-ethynyl-phenyl)amino]-6-{1-[(morpholin-4-yl)carbonyl]-piperidin-4-yloxy}-7-methoxy-quinazoline
4-[(3-chloro-4-fluoro-phenyl)amino]-6-{1-[(cis-2,6-dimethyl-morpholin-4-yl)carbonyl]-piperidin-4-yloxy}-7-methoxy-quinazoline
4-[(3-chloro-4-fluoro-phenyl)amino]-6-{1-[(2-methyl-morpholin-4-yl)carbonyl]-piperidin-4-yloxy}-7-methoxy-quinazoline
4-[(3-chloro-4-fluoro-phenyl)amino]-6-{1-[(S,S)-(2-oxa-5-azabicyclo[2,2,1]hept-5-yl)carbonyl]-piperidin-4-yloxy}-7-methoxy-quinazoline
4-[(3-chloro-4-fluoro-phenyl)amino]-6-{1-[(N-methyl-N-2-methoxyethylamino)carbonyl]-piperidin-4-yloxy}-7-methoxy-quinazoline
4-[(3-chloro-4-fluoro-phenyl)amino]-6-(1-ethyl-piperidin-4-yloxy)-7-methoxyquinazoline
4-[(3-chloro-4-fluoro-phenyl)amino]-6-{1-[(2-methoxyethyl)carbonyl]-piperidin-4-yloxy}-7-methoxy-quinazoline
4-[(3-chloro-4-fluoro-phenyl)amino]-6-{1-[(3-methoxypropyl-amino)carbonyl]-piperidin-4-yloxy}-7-methoxy-quinazoline
4-[(3-chloro-4-fluoro-phenyl)amino]-6-[cis-4-(N-methanesulphonyl-N-methylamino)-cyclohexan-1-yloxy]-7-methoxy-quinazoline
4-[(3-chloro-4-fluoro-phenyl)amino]-6-[cis-4-(N-acetyl-N-methyl-amino)cyclohexan-1-yloxy]-7-methoxy-quinazoline
4-[(3-chloro-4-fluoro-phenyl)amino]-6-(trans-4-methylamino-cyclohexan-1-yloxy)-7-methoxy-quinazoline
4-[(3-chloro-4-fluoro-phenyl)amino]-6-[trans-4-(N-methanesulphonyl-Nmethyl-amino)-cyclohexan-1-yloxy]-7-methoxy-quinazoline
4-[(3-chloro-4-fluoro-phenyl)amino]-6-(trans-4-dimethylamino-cyclohexan-1-yloxy)-7-methoxy-quinazoline
4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline
4-[(3-chloro-4-fluoro-phenyl)amino]-6-[2-(2,2-dimethyl-6-oxo-morpholin-4-yl)ethoxy]-7-[(S)-(tetrahydrofuran-2-yl)methoxy]-quinazoline
4-[(3-chloro-4-fluoro-phenyl)amino]-6-(1-methanesulphonyl-piperidin-4-yloxy)-7-methoxy-quinazoline
4-[(3-chloro-4-fluoro-phenyl)amino]-6-(1-cyano-piperidin-4-yloxy)-7-methoxy-quinazoline optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-ptoluenesulphonate.

The dopamine agonists used are preferably compounds selected from among bromocriptin, cabergoline, alpha-dihydroergocryptine, lisuride, pergolide, pramipexol, roxindol, ropinirol, talipexol, tergurid and viozan, optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-ptoluenesulphonate.

H1-Antihistamines which may be used are preferably compounds selected from among epinastine, cetirizine, azelastine, fexofenadine, levocabastine, loratadine, mizolastine, ketotifen, emedastine, dimetindene, clemastine, bamipine, cexchlorpheniramine, pheniramine, doxylamine, chlorophenoxamine, dimenhydrinate, diphenhydramine, promethazine, ebastine, desloratidine and meclozine, optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydroptoluenesulphonate.

It is also possible to use inhalable macromolecules, as disclosed in EP 1 003 478 A1 or CA 2297174 A1.

In addition, the compounds may come from the groups of ergot alkaloid derivatives, the triptans, the CGRP-inhibitors, the phosphodiesterase-V inhibitors, optionally in the form of the racemates, enantiomers or diastereomers thereof, optionally in the form of the pharmacologically acceptable acid addition salts, the solvates and/or hydrates thereof.

Examples of ergot alkaloid derivatives are dihydroergotamine and ergotamine.

| List of Reference Numbers | |
|---|---|
| 1 | inhaler |
| 2 | inhalation formulation |
| 3 | container |
| 4 | bag |
| 5 | pressure generator |
| 6 | holder |
| 7 | drive spring |
| 8 | locking element |
| 9 | conveying tube |
| 10 | nonreturn valve |
| 11 | pressure chamber |
| 12 | nozzle |
| 13 | mouthpiece |
| 14 | aerosol |
| 15 | air supply opening |
| 16 | upper housing part |
| 17 | inner part |
| 17a | upper part of the inner part |
| 17b | lower part of the inner part |
| 18 | housing part (lower part) |
| 19 | retaining element |
| 20 | jet |
| 21 | hole |
| 22 | plate |
| 23 | axis |
| 24 | outlet side |
| 25 | inlet side |
| 26 | intersection angle |
| 27 | distance of intersection form plate |
| 28 | cone or taper angle |
| 29 | diameter of hole |
| 30 | distance of holes |
| 31 | thickness |
| 32 | depression |
| 33 | angle of inclination |
| 34 | inlet region |

What is claimed is:

1. A nozzle for dispensing a fluid for inhalation, the nozzle comprising:
   a plate having only two holes, wherein the two holes are circular in cross section, have a hydraulic diameter between 5 and 15 μm, are formed perpendicular to a surface of the plate, taper towards an outlet side of the nozzle forming a natural cone with an essentially constant taper angle of about 5 to 20 degrees from an inlet side of the nozzle to the inlet side of the nozzle such that a diameter of the two holes at the outlet side is smaller than a diameter of the two holes at an inlet side of the nozzle wherein,
   the plate is deformed having a curved depression between two generally flat regions of the plate such that respective axes of the two holes intersect with each other at the outlet side of the nozzle so that respective jets of fluid exiting the two holes impact with each other at a position of impact when the fluid is dispensed, and
   the diameters and orientation of the two holes is such that impact of the respective jets of fluid generate an aerosol of a shape that expands significantly as a function of an increasing distance from the position of impact such that the resulting aerosol is suitable for patient inhalation of the dispensed fluid.

2. The nozzle according to claim 1, wherein the plate is made of metal.

3. The nozzle according to claim 1, wherein the plate has a thickness of less than 200 μm.

4. The nozzle according to claim 1, wherein the two holes are located on opposite sides of the curved depression.

5. The nozzle according to claim 1, wherein a distance between the two holes is about between 30 and 300 μm.

6. An inhaler for dispensing of an inhalation formulation as an aerosol, comprising:
   a conveying means for conveying a fluid from a source;
   a nozzle for dispensing the fluid for inhalation, the nozzle comprising a plate with only two holes, wherein the two holes are circular in cross section, have a hydraulic diameter between 5 and 15 μm, are formed perpendicular to a surface of the plate, taper towards an outlet side of the nozzle forming a natural cone with an essentially constant taper angle of about 5 to 20 degrees from an inlet side of the nozzle to the outlet side of the nozzle such that a diameter of the two holes at the outlet side is smaller than a diameter of the two holes at the inlet side of the nozzle, wherein:
   the plate is deformed having a curved depression between two generally flat regions of the plate such that respective axes of the two holes intersect with each other at the outlet side of the nozzle so that respective jets of fluid exiting the two holes impact with each other at a position of impact when the fluid is dispensed, and
   the diameters and orientation of the two holes is such that impact of the respective jets of fluid generate an aerosol of a shape that expands significantly as a function of an increasing distance from the position of impact such that the resulting aerosol is suitable for patient inhalation of the dispensed fluid.

* * * * *